United States Patent [19]

Rozen et al.

[11] Patent Number: 5,084,583
[45] Date of Patent: Jan. 28, 1992

[54] EPOXIDATION OF FLUORINE CONTAINING OLEFINS

[75] Inventors: Shlomo M. Rozen; Bruce E. Smart, both of Wilmington, Del.

[73] Assignee: E. I. Du Pont de Nemours and Company, Wilmington, Del.

[21] Appl. No.: 639,067

[22] Filed: Jan. 9, 1991

[51] Int. Cl.$^5$ .............................. C07D 303/08
[52] U.S. Cl. .................... 549/524; 549/523
[58] Field of Search ............ 549/523, 524, 526

[56] References Cited

U.S. PATENT DOCUMENTS 4,582,918  4/1986  Nagabhushan et al. ............ 549/525

OTHER PUBLICATIONS

Abstract of JP-136,107 (11/14/87).
Abstract of Russian Patent 390,084 (12/3/73).
Abstract of French Patent 2,529,890 (1/13/84).
Chemical Abstracts 88, 105112h (1978).
Rozen et al., Angew Chem. Int. Ed. Engl. 25, 6, 554 (1986).
Kirk-Othmer Encyclopedia of Chemical Technology, 3rd Ed., vol. 9, John Wiley & Sons, New York, pp. 251-266 (1980).
P. Tarrant et al., Fluorine Chemistry Reviews, vol. 5, Marcel Dekker Inc., New York, pp. 77-85 (1971).
D. Smith et al., Ind. Eng. Chem., vol. 49, pp. 1241-1246 (1957).

*Primary Examiner*—Glennon H. Hollrah
*Assistant Examiner*—Mark W. Russell

[57] ABSTRACT

The synthesis of epoxides from fluorine containing olefins using elemental fluorine in mixtures of water and acetonitrile is disclosed.

24 Claims, No Drawings

EPOXIDATION OF FLUORINE CONTAINING OLEFINS

This is a continuation of application Ser. No. 07/420,454, filed Oct. 12, 1989 now abandoned.

FIELD OF THE INVENTION

This invention relates to the synthesis of epoxides from fluorine-containing olefins using elemental fluorine in mixtures of water and acetonitrile.

BACKGROUND OF THE INVENTION

The epoxidation of olefins is a well known process practiced on a large industrial scale, for example see the Kirk-Othmer Encyclopedia of Chemical Technology, 3rd Ed., vol. 9, John Wiley & Sons, New York, 1980, p. 251-266. The most common method of epoxidation is the direct epoxidation of the olefin with an oxidizing agent such as a peracid, hydrogen peroxide or hypochlorous acid.

However, this method is usually not applicable to fluorinated olefins; other methods, which usually require more than one step, can be used to produce fluorine containing epoxides. These are reviewed by P. Tarrant, et al., in Fluorine Chemistry Reviews, vol. 5, Marcel Dekker, Inc., New York, 1971, p. 77-85, and specific examples are found in French Patent 2,529,890A, Japanese Patent 52-136,107 and USSR Patent No. 390,084. It is believed that the fluorinated olefins do not form epoxides in simple epoxidation reactions usually applicable to most olefins because of the electron deficient nature of the olefinic bond, caused by the presence of the fluorine atoms. This inability to undergo simple epoxidation reactions is illustrated hereinafter in Example 6.

S. Rozen and M. Brand, Angew. Chem. Int. Ed. Engl., vol. 25, 554-555 (1986) describe the direct epoxidation of olefins using a mixture of (elemental) fluorine, water and acetonitrile. The utility of this reaction with fluorinated olefins is neither discussed nor disclosed.

Fluorine containing epoxides are of special interest in polymer technology as they give rise to polymers with desirable properties. For example, D. D. Smith, et al., Ind. Eng. Chem., vol. 49, pg. 1241-1246 (1957), report such polymers are excellent low load lubricants. Thus a need exists for a direct efficient epoxidation process for fluorine containing olefins.

It is therefore an object of the present invention to provide a process for the direct epoxidation of fluorine containing olefins.

SUMMARY OF THE INVENTION

The present invention comprises a process for direct epoxidation of fluorinated olefins wherein first an oxidizing reagent is created by passing elemental fluorine through a mixture of acetonitrile and water, and then a fluorine containing olefin is contacted with the oxidizing solution to yield the desired epoxide.

DETAILED DESCRIPTION OF THE INVENTION

When diluted fluorine is passed through a cold mixture of acetonitrile-water an oxidizing reagent, stable at temperatures of up to 25° C. for several hours, is formed. Unlike other direct epoxidation methods, this oxidizing reagent can be used to epoxidize the much more inert and resistant polyfluorinated olefins.

Fluorine is of course a strong oxidizer and a very corrosive material. An appropriate vacuum line made from copper or monel in a well ventilated area should be constructed for working with this element. The epoxidation reactions themselves can be carried out in glass vessels.

Fluorinated olefins suitable for use in the epoxidation process of the present invention include those of formula (I) and (II) as follows:

wherein Z is $ACF_2—$, or perfluoroaryl;
Y is

or perfluoroaryl;
A is perfluoroalkyl fluorine, hydrocarbyl, or substituted hydrocarbyl; and
B is fluorine or perfluoroalkyl.

Suitable substituents when A is substituted hydrocarbyl include the vinyl group, $CH_2=CH—$, and any substituent inert under the reaction conditions of the process and which does not interfere with the process. When the vinyl group, $H_2C=CH—$, is present it too will be epoxidized, assuming enough oxidizing reagent is used. Inert substituents also include groups between hydrocarbyl segments such as ethers. Examples of suitable substituents include chlorine, fluorine, esters, ethers, and ketones.

Preferred fluorine containing olefins for use herein include those of formula (I) wherein Z is $ACF_2—$, or perfluoroaryl, and A is perfluorohydrocarbyl and those of formula (II) wherein Y is

or perfluoroaryl, A is perfluorohydrocarbyl, and B is fluorine. Olefins of the formula (I) wherein Z is $ACF_2$ and A is perfluoro-n-alkyl or of formula (II) wherein Y is

A is perfluoro-n-alkyl and B is fluorine are most preferred. In another preferred embodiment, Z is $ACF_2—$, and A is $CH_2=CH(CF_2)_n—$, wherein n is an integer from 0 to about 30.

Fluorinated olefins useful in the present process include, but are not limited to (perfluoropropyl)ethylene, 3,3,3-trifluoropropene, (perfluorobutyl)ethylene, (perfluorohexyl)ethylene, 9,10-dichloro-3,3,4,4,6,7,7,9,10,10-decafluoro-5-trifluoromethyl-5,8-dioxa-1-decene, pentafluoro-phenylethylene, 3-(perfluorohexyl)propene, 3-(perfluorooctyl)propene, 3-(perfluorooctadecyl)propene, and 3,3-difluorocyclohexene, 3-pentafluorophenylpropane and 3,3,4,4,5,5,6,6,7,7,8,8-dodecafluoro-1,9-decene.

The reaction proceeds according to the following equations:

A. 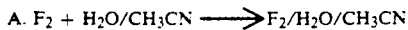

B1. 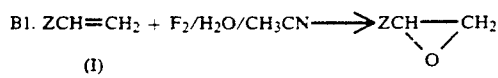

(I)

or

B2. $YCH_2CH=CH_2 + F_2/H_2O/CH_3CN \longrightarrow$ (II)

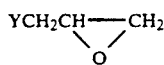

A suitable temperature range for the process of the present invention is from about −15° C. to about 30° C. Preferably the reaction is conducted at from about 0° C. to about 25° C. Reaction times can range from about 1 minute to 3 or more hours. A typical reaction time is from about 2 to 3 hours. The desired product may be isolated via extraction followed by distillation or evaporation of the solvent.

Mixtures of up to 25%, preferably 10-15% fluorine diluted with an inert gas such as nitrogen are used in the preparation of the oxidizing reagent. The gas mixtures are usually prepared in a secondary container before passing into the water/acetonitrile mixture. The gas mixture is then passed at a rate of about 400 ml per minute through a cold (−10° C.) and vigorously stirred mixture of acetonitrile and water. The ratio of acetonitrile to water is about 10:1, for example 400 ml of acetonitrile and 40 ml of water. The formation of the oxidizing reagent can be monitored by reacting aliquots with acidic aqueous solution of potassium iodide. The liberated iodine is then titrated with thiosulfate. Concentrations of more than one mol/liter of oxidizing reagent have been obtained.

The oxidizing reagent is then contacted with a suitable fluorinated olefin to obtain the desired epoxide. An appropriate amount of olefin is dissolved in solvent such as methylene chloride, chloroform, or a fluorocarbon, cooled to about 0° C., and added in one portion to the reaction vessel containing the oxidizing agent. The solvent should be inert under process conditions. For example, most unsaturated solvents, such as hexene and toluene, react with the oxidizing reagent, and should be avoided. A 6-10 fold excess of the oxidizing reagent is employed. Except in the case of the more reactive olefins, the cooling bath is removed and the reaction stopped after about 3 hours by neutralizing it with saturated sodium bicarbonate solution. It should be noted that the reaction could be conducted much longer, but since most of the oxidizing reagent is decomposed after 2 to 3 hours, little additional product is obtained. A yield of about 70-80% of the epoxide can be obtained in about 80% conversion. The reaction mixture can then be poured into water, extracted with an organic solvent such as $CFCl_3$, and neutralized, usually by washing with sodium bicarbonate and then water. The organic layer is dried, typically over anhydrous $MgSO_4$, and the solvent distilled, preferably at atmospheric pressure. The crude product is usually distilled under reduced pressure.

The following Examples 1-5 demonstrate the process of the present invention, but are not intended to limit it in any manner. The following Example 6 demonstrates that fluorine containing olefins do not undergo the typical simple epoxidation reactions known in the art.

EXAMPLE 1

Epoxidation of (Perfluorobutyl)ethylene

Oxidizing solution containing 250 mmol of oxidant was made by preparing a solution of 400 ml of $CH_3CN$ and 40 ml of $H_2O$ which was then cooled to −10° C. Then 10% fluorine in nitrogen was bubbled through the hollow shaft of a vibromixer equipped with a stirring disk (from Chemap AG), which causes vigorous stirring and the formation of fine gas bubbles. Aliquots were periodically withdrawn and titrated as previously described for oxidizing reagent. A final total of 360 mmoles of oxidizing agent was formed. To this solution 15 g (61 mmol) of (perfluorobutyl)ethylene dissolved in 30 ml $CH_2Cl_2$ was added. The reaction was left overnight and poured into 1.5 l of water and extracted 3 times with 200 ml of $CFCl_2$. The organic layer was then neutralized with sodium bicarbonate solution, washed with water and dried over anhydrous $MgSO_4$. The organic solvent was removed by distillation through an efficient distillation column. The epoxide was then distilled to give 3 g of the starting material and about 10 g of the epoxide; b.p.=81°-83° C.; IR=1240 cm$^{-1}$; $^1$H NMR=3.0 (2H, d of narrow m, J=10 Hz), 3.5 ppm (1H, t of narrow m, J=10 Hz), $^{19}$F NMR=−81.6 ppm (3F, t of narrow m, J=10 Hz); MS m/e=262 (M+).

EXAMPLE 2

Epoxidation of (Perfluorohexyl)ethylene

The oxidizing reagent (230 mmol) was prepared in 440 ml of $CH_3CN/H_2O$ solution (10:1) as in Example 1. Then 20 g of (perfluorohexyl)ethylene was dissolved in 20 ml of $CH_2Cl_2$ and added to the oxidizing reagent solution. After 2 h the reaction was neutralized with bicarbonate. Then 230 ml of the reaction mixture was distilled at 80 mm. This cut consisted mainly of acetonitrile and the desired epoxide. It was poured into 1 liter water and worked up as above in Example 1. The epoxide (80% yield at 60% conversion) was distilled at 20°-22° C. at 1 mm. IR =1200, 1240 cm$^{-1}$; $^1$H NMR=3.0 (2H, d of narrow m, J =10 Hz), 3.5 ppm (1H, t of narrow m, J=10 Hz); $^{19}$F NMR=−81.4 ppm (3F, t of narrow m, J=10 Hz); MS m/e=362 (M+).

EXAMPLE 3

Epoxidation of (Pentafluorophenyl)ethylene

The oxidizing reagent (100 mmol) was prepared in 440 ml of $CH_3CN/H_2O$ solution (10:1) as in Example 1. The 8 g of (pentafluorophenyl)ethylene was dissolved in 20 ml of $CH_2Cl_2$ and added to the reagent solution. After 5 min the reaction was neutralized with bicarbonate. Most of the liquids were distilled under reduced pressure (80 mm). The remaining liquid (50 ml) was poured into water, extracted with $CFCl_3$ and worked-up as in Example 1. The epoxide was distilled at 34°-37° C. at 0.1 # mm; yield 6.7 g (85%). $^1$H NMR=3.2 (2H, 2 narrow m), 4.0 ppm (1H, narrow m); $^{19}$F NMR=−143.9 (2F, m), −154.1 (1F, t, J=21 Hz), −162.5 ppm (2F, m); MS m/e=210 (M+).

EXAMPLE 4

Epoxidation of a Mixture of "Allyl Telomers"

The oxidizing reagent (100 mmol) was prepared in 440 ml of $CH_3CN/H_2O$ solution (10:1) as in Example 1. Then 20 g of 1:1:1 mixture (molar) of $C_6F_{13}CH_2CH=CH_2$, $C_8F_{17}CH_2CH=CH_2$ and $C_{10}F_{21}CH_2CH=CH_2$ was dissolved in 50 ml of $CH_2Cl_2$ and added to the reagent solution. After 10 min the reaction was neutralized with bicarbonate. The reaction mixture was poured into water, extracted with $CFCl_3$ and worked-up as in Example 1. The 16.3 g of the respective epoxide mixture (1:1:1) obtained was practically pure.

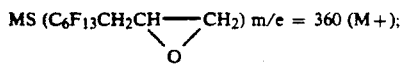

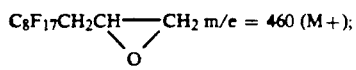

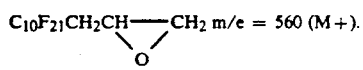

EXAMPLE 5

Epoxidation of a Diene

Using a procedure similar to that in Example 1, a solution of 240 mmoles of oxidizing reagent was prepared in 440 mL of acetonitrile/water (10:1) solution. To this solution was added 10 g of 3,3,4,4,5,5,6,6,7,7,8,8,9,9,10,10,11,11,12,12-eicosa-fluorotetradeca-1,13-diene dissolved in 30 mL of $CH_2Cl_2$. After standing overnight at room temperature the reaction was worked up in a similar manner to Example 1, by being neutralized with bicarbonate, poured into water, extracted with $CFCl_3$, and dried over anhydrous magnesium sulfate. The solvent was evaporated under reduced pressure. GC/MS analysis showed that both the mono- and bisepoxides were obtained in 30% and 55% yields, respectively. The reaction can be repeated on this crude product to increase the yield of the bisepoxide. $^1H$ NMR of the bisepoxide: 3.5 ppm (1H, 3 narrow m), 3.0 ppm (2H, m). MS, m/e (bisepoxide): 586 (M+), 536 (M+-$CF_2$), 486 (M+-2$CF_2$), 100 [($CF_2$)$_2$]+. MS, m/e (monoepoxide): 551 (M+-F), 77 ($CF_2CH=CH_2$)+.

EXAMPLE 6

Attempted Epoxidation of (Perfluorobutyl)ethylene by Trifluoroperacetic Acid

A mixture of 5.7 mL (0.1 mol) of 50% $H_2O_2$ and 50 mL of methylene chloride was stirred at 0°-10° C. while there was added dropwise 42.4 mL (63 g, 0.3 mol) of trifluoroacetic anhydride. The cold mixture was stirred for 10 min., then treated at 0° C. with a solution of 24.6 g (0.10 mol) of (perfluorobutyl)ethylene in 50 mL of methylene chloride. No exotherm was discerned. The homogeneous mixture was refluxed for two hours while slow gas evolution occurred. Analysis of the cooled solution by GC showed $CF_3CF_2CF_2CF_2CH=CH_2$, $CH_2Cl_2$ and $CF_3CO_2H$ to be present, but no epoxidized (perfluorobutyl)ethylene.

What is claimed is:

1. A process for direct epoxidation of fluorine containing olefins comprising:
   (A) generating an oxidizing reagent by passing fluorine through a mixture of acetonitrile and water; and
   (B) contacting a fluorine containing olefin in a solvent with the oxidizing reagent to yield the desired epoxide; wherein the fluorine containing olefin comprises a compound of formula (I) or (II)

$ZCH=CH_2$ (I)

$YCH_2CH=CH_2$ (II)

wherein
   Z is $ACF_2-$, or perfluoroaryl;

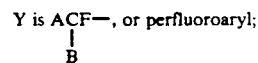

A is perfluoroalkyl, fluorine, hydrocarbyl, or fluorine substituted hydrocarbyl; and
   B is fluorine or perfluoroalkyl.

2. The process of claim 1 wherein Z is

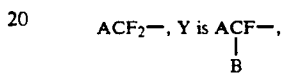

and A is perfluorohydrocarbyl.
3. The process of claim 2 wherein B is fluorine.
4. The process of claim 2 wherein A is perfluoroalkyl.
5. The process of claim 4 wherein A is perfluoro-n-alkyl.
6. The process of claim 5 wherein B is fluorine.
7. The process of claim 1 wherein the olefin is (perfluorohexyl)ethylene.
8. The process of claim 1 wherein the olefin is (pentafluorophenyl)ethylene.
9. The process of claim 1 wherein the olefin is (perfluorobutyl)ethylene.
10. The process of claim 1 wherein the olefin comprises a mixture of allyl telomers.
11. The process of claim 1 wherein the fluorine is diluted with nitrogen prior to contact with the mixture of acetonitrile and water.
12. The process of claim 11 wherein the ratio of acetonitrile to water is about 10:1.
13. The process of claim 12 wherein the mixture of acetonitrile and water is cooled to a temperature of about 10° C. prior to contact with the fluorine.
14. The process of claim 13 wherein the fluorine is passed at a rate of about 400 ml per minute through the mixture of acetonitrile and water.
15. The process of claim 1 wherein the fluorine containing olefin is dissolved in a solvent selected from methylene chloride, chloroform, or a fluorocarbon.
16. The process of claim 1 wherein the fluorine containing olefin is contacted with a 6-10 fold excess of the oxidizing reagent.
17. The process of claim 16 wherein the epoxidation is conducted at a temperature of from about $-15°$ C. to 30° C.
18. The process of claim 17 wherein the epoxidation is conducted at a temperature of from about 0° C. to about 25° C.
19. The process of claim 18 wherein the reaction time is from about 1 minute to about 3 hours.
20. The process of claim 18 wherein the fluorine containing olefin comprises $ACF_2CH=CH_2$ wherein A is perfluoro-n-alkyl.
21. The process of claim 18 wherein the fluorine containing olefin comprises

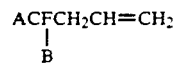
wherein A is perfluoro-n-alkyl and B is fluorine.
22. The process of claim 1 wherein Z and Y are independently perfluoroaryl.
23. The process of claim 1 wherein Z is $ACF_2-$, A is $CH_2=CH(CF_2)_n-$, and n is an integer from 0 to about 30.
24. The process of claim 18 wherein Z is $ACF_2-$, A is $CH_2=CH(CF_2)_n-$, and n is an integer from 0 to about 30.
* * * * *